United States Patent
Maiden et al.

(10) Patent No.: US 9,448,160 B2
(45) Date of Patent: Sep. 20, 2016

(54) METHOD AND APPARATUS FOR PROVIDING IMAGE DATA FOR CONSTRUCTING AN IMAGE OF A REGION OF A TARGET OBJECT

(75) Inventors: Andrew Michael Maiden, Sheffield (GB); Martin James Humphry, Sheffield (GB)

(73) Assignee: PHASE FOCUS LIMITED, Sheffield, South Yorkshire (GB)

(*) Notice: Subject to any disclaimer, the term of this patent is extended or adjusted under 35 U.S.C. 154(b) by 58 days.

(21) Appl. No.: 14/114,086

(22) PCT Filed: Apr. 27, 2012

(86) PCT No.: PCT/GB2012/050929
§ 371 (c)(1),
(2), (4) Date: Oct. 25, 2013

(87) PCT Pub. No.: WO2012/146929
PCT Pub. Date: Nov. 1, 2012

(65) Prior Publication Data
US 2014/0043616 A1    Feb. 13, 2014

(30) Foreign Application Priority Data
Apr. 27, 2011  (GB) .................................. 1107053.9

(51) Int. Cl.
*G01N 21/05* (2006.01)
*G06T 1/00* (2006.01)

(52) U.S. Cl.
CPC .............. *G01N 21/05* (2013.01); *G06T 1/0007* (2013.01); *G06T 2207/20208* (2013.01)

(58) Field of Classification Search
CPC ................... G06T 2207/20208; G01N 21/05

USPC .......... 382/294, 103, 244–247; 356/442–446
See application file for complete search history.

(56) References Cited

U.S. PATENT DOCUMENTS 5,570,180 A   10/1996 Nagai
6,809,829 B1  10/2004 Takata et al.
(Continued)

FOREIGN PATENT DOCUMENTS

CN   101820817 A   9/2010
EP       1832930     9/2007
(Continued)

OTHER PUBLICATIONS

United Kingdom Search Report dated Aug. 11, 2011, Great Britain Application No. GB1107053.9, pp. 1-2.
(Continued)

*Primary Examiner* — Kara E Geisel
*Assistant Examiner* — Dominic J Bologna
(74) *Attorney, Agent, or Firm* — MH2 Technology Law Group, LLP

(57) ABSTRACT

Embodiments of the present invention provide a method (200) of providing image data for constructing an image of a region of a target object, comprising detecting, by at least one detector (40), at least a portion of radiation scattered by a target object (30) with the incident radiation (10) or an aperture at a predetermined probe position, determining an offset vector (203) for reducing an error associated with the probe position (201), estimating a wavefront (210) based on a probe function having the offset vector applied to the probe position, and providing image data responsive to the detected radiation.

32 Claims, 6 Drawing Sheets

(56) References Cited

U.S. PATENT DOCUMENTS

| | | | |
|---|---|---|---|
| 6,809,845 | B1 | 10/2004 | Kim et al. |
| 7,298,497 | B2 | 11/2007 | Millerd et al. |
| 7,734,084 | B2* | 6/2010 | Stewart .............. G06K 9/3216 382/151 |
| 2003/0202634 | A1 | 10/2003 | Gerchberg |
| 2004/0145747 | A1 | 7/2004 | Jasapara |
| 2005/0280813 | A1 | 12/2005 | Jones et al. |
| 2007/0252975 | A1 | 11/2007 | Liang |
| 2008/0048102 | A1 | 2/2008 | Kurtz et al. |
| 2008/0095312 | A1* | 4/2008 | Rodenburg .......... G01T 1/2914 378/87 |
| 2010/0135534 | A1 | 6/2010 | Weston et al. |
| 2010/0165355 | A1 | 7/2010 | Kato |
| 2011/0085173 | A1 | 4/2011 | Waller et al. |
| 2011/0116081 | A1 | 5/2011 | Sugimoto |
| 2011/0134438 | A1 | 6/2011 | Kato |
| 2011/0292379 | A1 | 12/2011 | Kato |
| 2013/0033703 | A1 | 2/2013 | Humphry et al. |
| 2013/0092816 | A1 | 4/2013 | Barrett et al. |
| 2013/0181990 | A1 | 7/2013 | Rodenburg et al. |

FOREIGN PATENT DOCUMENTS

| | | |
|---|---|---|
| EP | 2063260 | 5/2009 |
| EP | 2233905 | 9/2010 |
| GB | 2403616 A | 1/2005 |
| GB | 2481589 | 1/2012 |
| JP | 2005106835 | 4/2005 |
| JP | 2006-314643 A | 11/2006 |
| JP | 2007-526069 A | 9/2007 |
| JP | 2007-534956 A | 11/2007 |
| JP | 2010-528764 A | 8/2010 |
| JP | 2010-204755 A | 9/2010 |
| JP | 2012-511147 A | 5/2012 |
| WO | 96/38722 | 12/1996 |
| WO | 2004/113856 | 12/2004 |
| WO | 2005/106531 | 11/2005 |
| WO | 2005/106531 A1 | 11/2005 |
| WO | 2010/035033 A1 | 4/2010 |
| WO | 2010/064051 | 6/2010 |
| WO | 2010/119278 A1 | 10/2010 |
| WO | 2011/033287 A1 | 3/2011 |
| WO | 2011/131981 | 10/2011 |
| WO | 2011/149000 | 12/2011 |

OTHER PUBLICATIONS

Martin Dierolf et al., "Coherent laser scanning diffraction microscopy", Journal of Physics: Conference Series, vol. 186, 2009, pp. 1-3.
Andreas Menzel et al , "Advances in Ptychographical Coherent Diffractive Imaging", Proceedings of SPIE, vol. 7076, 2008, pp. 707609-01-707609-08.
Cameron M. Kewish et al., "Ptychographic characterization of the wavefield in the focus of reflective hard X-ray optics", Ultramicroscopy, vol. 110, 2010, pp. 325-329.
Pierre Thibault et al., "Probe retrieval in ptychographic coherent diffractive imaging", Ultramicroscopy, vol. 109, 2009, pp. 338-343.
International Search Report dated Aug. 17, 2012, International Application No. PCT/GB2012/050929 filed Apr. 27, 2012, pp. 1-4.
International Search Report and Written Opinion of the International Searching Authority dated Feb. 10, 2014, International Application No. PCT/GB2013/050155 filed Jan. 24, 2013, pp. 1-18.
D. Claus et al., "Ptychography: A novel phase retrieval technique, advantages and its application", Proceedings of SPIE, vol. 8001, 2011, pp. 800109-1-800109-6.
Richard M. Goldstein et al., "Satellite radar interferometry: Two-dimensional phase unwrapping", Radio Science, vol. 23, No. 4, 1988, pp. 713-720.
United Kingdom Search Report dated May 30, 2012, Great Britain Application No. GB1201140.9, pp. 1-5.
United Kingdom Search Report dated Oct. 3, 2012, Great Britain Application No. GB1201140.9, pp. 1-3.
International Preliminary Report on Patentability dated Nov. 4, 2014, International Application No. PCT/GB2013/051168 filed May 3, 2013, pp. 1-8.
International Search Report dated Aug. 5, 2013, International Application No. PCT/GB2013/051168, pp. 1-3.
United Kingdom Search Report dated May 3, 2013, Great Britain Application No. GB1207800.2, pp. 1-7.
Martin Dierolf et al., "Ptychography & Lensless X-Ray Imaging", Europhysics News, vol. 39, No. 1, 2008, pp. 22-24.
Oliver Bunk et al., "Influence of the Overlap Parameter on the Convergence of the Ptychographical Iterative Engine", Ultramicroscopy, vol. 108, 2008, pp. 481-487.
International Preliminary Report on Patentability dated Jun. 13, 2013, International Application No. PCT/GB2011/052392 filed Dec. 2, 2011, pp. 1-7.
International Search Report dated Jun. 13, 2012, International Application No. PCT/GB2011/052392 filed Dec. 2, 2011, pp. 1-5.
Intellectual Property Office Search Report dated Apr. 11, 2011, United Kingdom Application No. GB1020516.9, pp. 1-4.
H. M. L Faulkner et al., "Error tolerance of an iterative phase retrieval algorithm for movable illumination microscopy", Ultramicroscopy, vol. 103, 2005, pp. 153-164.
Andrew M. Maiden et al., "Superresolution imaging via ptychography", Journal of the Optical Society of America A, vol. 28, No. 4, Apr. 2011, pp. 604-612.
R. W. Gerchberg, "Super-resolution through error energy reduction", Optica ACTA, vol. 21, No. 9, Jan. 1974, pp. 709-720.
Manuel Guizar-Sicairos et al., "Phase retrieval with Fourier-weighted projections", Journal of the Optical Society of America A, vol. 25, No. 3, Mar. 2008, pp. 701-709.
Maiden, A. M. et al. An improved ptychographical phase retrieval algorithm for diffractive imaging. Ultramicroscopy, Sep. 2009, vol. 109, No. 10, pp. 1256-1262.
Guizar-Sicairos, M. et al. Phase retrieval with transverse translation diversity: a nonlinear optimization approach. Optics Express, May 12, 2008, vol. 16, No. 10, pp. 7264-7278.
"Written Opinion of the International Searching Authority," dated Oct. 27, 2013 for PCT Int'l Appl. No. PCT/GB2012/050929 filed Apr. 27, 2012, pp. 1-11.
Non-Final Office Action dated Jun. 18, 2015, U.S. Appl. No. 14/374,157, pp. 1-25.
Notification of Reasons for Refusal dated Jun. 11, 2015, Japanese Application No. 2013-541430, pp. 1-4 (including English Language Translation).
Non-Final Office Action dated Jan. 21, 2016, for U.S Appl. No. 14/398,391, pp. 1-42.
First Office Action dated Mar. 3, 2016, Chinese Application No. 201280020664.3, pp. 1-8 (including English Language Summarization).
Japanese Office Action dated Feb. 16, 2016, Japanese Application No. 2014-506932, pp. 1-6 (including English Language Translation).
F. Hue et al., "Extended ptychography in the transmission electron microscope: Possibilities and limitations", Ultramicroscopy, vol. 111, 2011, pp. 1117-1123.
A. M. Maiden, "An annealing algorithm to correct positioning errors in ptychography", Ultramicroscopy, vol. 120, 2012, pp. 64-72.
Final Office Action dated Jul. 21, 2016, U.S. Appl. No. 14/398,391, pp. 1-35.

* cited by examiner (a)          (b)

METHOD AND APPARATUS FOR PROVIDING IMAGE DATA FOR CONSTRUCTING AN IMAGE OF A REGION OF A TARGET OBJECT

CROSS-REFERENCE TO RELATED APPLICATIONS

This application is a U.S. National Stage application of International Application No. PCT/GB2012/050929 filed 27 Apr. 2012, which claims priority to Great Britain patent application 1107053.9 filed 27 Apr. 2011, the entire disclosures of which are hereby incorporated herein by reference in their entireties.

BACKGROUND

The present invention relates to methods and apparatus for providing image data from which an image of at least a portion of a target object may be generated. In particular, embodiments of the invention relate to methods and apparatus for improving a quality of image data.

WO 2005/106531, which is incorporated herein by reference for all purposes, discloses a method and apparatus of providing image data for constructing an image of a region of a target object. Incident radiation is provided from a radiation source at the target object. An intensity of radiation scattered by the target object is detected using at least one detector. The image data is provided responsive to the detected radiation. A method for providing such image data via an iterative process using a moveable softly varying probe function such as a transmittance function or illumination function is also disclosed. The methods and techniques disclosed in WO 2005/106531 are referred to as a ptychographical iterative engine (PIE).

PIE provides for the recovery of image data relating to at least an area of a target object from a set of diffraction pattern measurements. Several diffraction patterns are recorded at a measurement plane using one or more detectors, such as a CCD or the like. A probe function, which might be a transmittance function associated with a post-target object aperture or an illumination function, must be known or estimated.

WO 2010/064051, which is incorporated herein by reference for all purposes, discloses an enhanced PIE (ePIE) method wherein it is not necessary to know or estimate the probe function. Instead a process is disclosed in which the probe function is iteratively calculated step by step with a running estimate of the probe function being utilised to determine running estimates of an object function associated with a target object.

Other methods of providing image data based on measurement of scattered radiation are also known.

In such methods, movement between a plurality positions is often required. In some methods, the movement is relative movement between the object and the radiation or probe. To achieve such movement, the object, probe or both may be moved amongst a plurality of positions. The probe may be moved by altering a position of the radiation source, focussing optics or an aperture. The accuracy of such movements presents a limitation on the accuracy of the resultant image data.

It is an object of embodiments of the invention to at least mitigate one or more of the problems of the prior art.

SUMMARY OF THE INVENTION

According to a first aspect of the present invention there is provided a method of providing image data for constructing an image of a region of a target object, comprising detecting, by at least one detector, at least portion of radiation scattered by a target object with the incident radiation or an aperture at a predetermined probe position; determining an offset vector for reducing an error associated with the probe position; estimating a wavefront based on a probe function having the offset vector applied to the probe position; and providing image data responsive to the detected radiation.

Optionally, the method may further comprise estimating at least one of an object function indicating at least one characteristic of at least a region of the target object and/or the probe function indicating at least one characteristic of incident radiation at the target object or the aperture. The method may include estimating a wave front at a plane of the at least one detector based on the object function and the probe function. A portion of the wave front may be based on the detected radiation. A portion of the estimated wave front may be left substantially unchanged. The updating of the wave front or the portion of the wave front may comprise updating a modulus of the wave front according to the detected radiation. The wave front or the portion of the wave front may be updated with:

$$\sqrt{I_{s(j)}(u)}$$

where $I_{s(j)}(u)$ a detected intensity of radiation for a probe position j.

The method may comprise determining an ordering of the positions of the incident radiation or the aperture for the measurements of the portion of scattered radiation to be used in the iterative process. The determined ordering may be random or pseudo-random. The ordering may be a non-sequential pattern.

Optionally, the method may comprise detecting an intensity of radiation scattered by the target object with the incident radiation or the post target aperture at a first position with respect to the target object. The incident radiation or the post-target aperture may be repositioned at at least one further position relative to the target object. Subsequently, the method may comprise detecting the intensity of radiation scattered by the target object with the incident radiation or post-target aperture at the at least one further position.

Optionally, the method may comprise estimating an object function indicating at least one characteristic of said region of the target object; and/or estimating the probe function indicating at least one characteristic of incident radiation at the target object or the post-target aperture; and iteratively re-estimating each of the object function and/or probe function.

Optionally, the method may comprise multiplying the estimated object function by the estimated probe function to thereby provide an exit wave function; propagating the exit wave function to provide an estimate of an expected scattering pattern or wave front at the detector; and correcting at least one characteristic of said expected scattering pattern according to a detected intensity of radiation scattered by the target object.

Optionally, the method may comprise inversely propagating a corrected expected scattering pattern to thereby provide an updated exit wave function.

Optionally, the method may comprise propagating the estimated probe function to provide an estimate scattering pattern in a measurement plane of the detector where the propagation operator $\mathcal{T}$ suitably models the propagation between the plane of the object and the measurement plane. $\mathcal{T}$ may comprise a Fourier Transform or a Fresnel Transform.

Optionally, the method may comprise updating a running estimate of the probe function and/or a running estimate of an object function simultaneously with each iteration of the method.

Optionally, the method may further comprise providing an initial estimate of the probe function as a prior modelled probe function. The initial estimate of the probe function may be provided by a random approximation for the probe function.

Optionally, wherein the target object may be at least partially transparent to the incident radiation and detecting an intensity of radiation scattered by the target object may comprise detecting an intensity of radiation transmitted by the target object.

Optionally, the target object may be at least partially reflective to the incident radiation and detecting an intensity of radiation scattered by the target object may comprise detecting an intensity of radiation reflected by the target object.

According to a second aspect of the present invention there is provided an apparatus for providing image data for constructing an image of a region of a target object, comprising a data store storing data indicating an intensity of radiation scattered by a target object with the incident radiation or an aperture at a predetermined probe position, and a processing means arranged to determine an offset vector for reducing an error associated with the probe position, estimate a wavefront based on a probe function having the offset vector applied to the probe position, and to provide image data responsive to the detected radiation.

The apparatus may optionally comprise at least one detector for detecting an intensity of radiation scattered by the target object. The processing means may be arranged to provide image data via an iterative process responsive to the detected radiation object with incident radiation or an aperture at first and second positions, wherein in said iterative process image data is provided corresponding to a portion of radiation scattered by the target object and not detected by the detector.

The processing means may be arranged to provide image data via an iterative process responsive to the detected radiation with incident radiation or an aperture at first and second positions, wherein in said iterative process image data is provided corresponding to a portion of radiation scattered by the target object and not detected by the detector.

The processing means may be arranged to estimate at least one of an object function indicating at least one characteristic of at least a region of the target object and/or the probe function indicating at least one characteristic of incident radiation at the target object or the aperture. The processing means may further be arranged to estimate a wave front at a plane of the at least one detector based on the object function and the probe function. The processing means may be further arranged to update the wave front or a portion of the wave front based on the detected radiation and leaving a portion of the estimated wave front substantially unchanged.

The processing means may be arranged to update a modulus of wave front or the portion of the wave front according to the detected radiation.

According to a further aspect of the present invention there is provided a computer program which, when executed by a computer, performs a method of providing image data for constructing an image of a region of a target object, comprising detecting, by at least one detector, at least a portion of radiation scattered by a target object with the incident radiation or an aperture at a predetermined probe position, determining an offset vector for reducing an error associated with the probe position, estimating a wavefront based on a probe function having the offset vector applied to the probe position, and providing image data responsive to the detected radiation.

Embodiments of the invention provide image data having an improved resolution. Some embodiments of the invention improve a rate of convergence a method of determining the image data. Some embodiments of the invention reduce a noise present in the image data. Further aspects of the invention will be appreciated from the description which follows and the appended claims.

BRIEF DESCRIPTION OF THE DRAWINGS

Embodiments of the invention will now be described by way of example only, with reference to the accompanying figures, in which.

DETAILED DESCRIPTION OF EMBODIMENTS OF THE INVENTION

Figure 1:
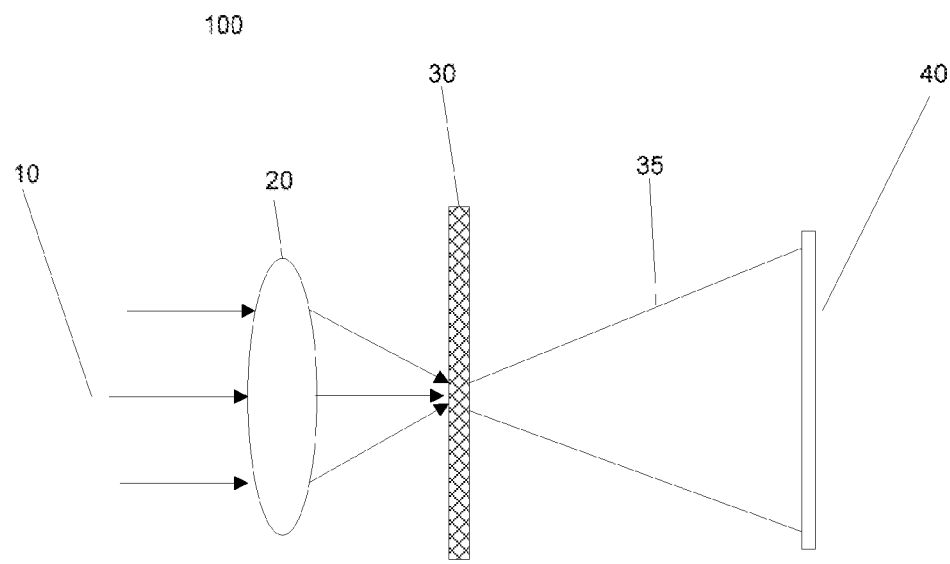
FIG. 1 shows an apparatus according to an embodiment of the invention.

FIG. 1 illustrates an apparatus 100 according to an embodiment of the invention. The apparatus is suitable to provide image data of an object which may, although not exclusively, be used to produce an image of at least a region of the object.

A radiation source, which although not shown in FIG. 1, is a source of radiation 10 which falls upon a focusing arrangement 20, such as one or more lenses, and is caused to illuminate a region of a target object 30. It is to be understood that the term radiation is to be broadly construed. The term radiation includes various wave fronts. Radiation includes energy from a radiation source. This will include electromagnetic radiation including X-rays, emitted particles such as electrons. Other types of radiation include acoustic radiation, such as sound waves. Such radiation may be represented by a wave function $\Psi(r)$. This wave function includes a real part and an imaginary part as will be understood by those skilled in the art. This may be represented by the wave functions modulus and phase. $\Psi(r)^*$ is the complex conjugate of $\Psi(r)$ and $\Psi(r)\Psi(r)^* = |\Psi(r)|^2$ where $|\Psi(r)|^2$ is an intensity which may be measured for the wave function.

The lens 20 forms a probe function $P(r)$ which is arranged to select a region of the target object 20 for investigation. The probe function selects part of an object exit wave for analysis. P(r) is the complex stationary value of this wave field calculated at the plane of the object 40.

It will be understood that rather than weakly (or indeed strongly) focusing illumination on the target 40, unfocused radiation can be used with a post target aperture. An aperture is located post target object to thereby select a region of the target for investigation. The aperture is formed in a mask so that the aperture defines a "support". A support is an area of a function where that function is not zero. In other words outside the support the function is zero. Outside the support the mask blocks the transmittance of radiation. The term aperture describes a localised transmission function of radiation. This may be represented by a complex variable in two dimensions having a modulus value between 0 and 1. An example is a mask having a physical aperture region of varying transmittance.

Incident radiation thus falls upon the up-stream side of the target object 30 and is scattered by the target object 30 as it is transmitted. The target object 30 should be at least partially transparent to incident radiation. The target object 30 may or may not have some repetitive structure. Alternatively the target object 30 may be wholly or partially reflective in which case a scattering pattern is measured based on reflected radiation.

A specimen wave O(r) is thus formed as an exit wave function of radiation after interaction with the object 30. In this way O(r) represents a two-dimensional complex function so that each point in O(r), where r is a two-dimensional coordinate, has associated with it a complex number. O(r) will physically represent an exit wave that would emanate from the object which is illuminated by a plane wave. For example, in the case of electron scattering, O(r) would represent the phase and amplitude alteration introduced into an incident wave as a result of passing through the object 30 of interest. The probe function P(r) (or transmission function) selects a part of the object exit wave function for analysis. It will be understood that rather than selecting an aperture a transmission grating or other such filtering function may be located downstream of the object function. The probe function P(r-R) is an aperture transmission function where an aperture is at a position R. The probe function can be represented as a complex function with its complex value given by a modulus and phase which represent the modulus and phase alterations introduced by the probe into a perfect plane wave incident up it. It will also be understood that both the probe and specimen functions may be three-dimensional complex functions, P(s) and O(s), so that each point in P(s) and O(s), where s is a three-dimensional coordinate, has associated with it a complex number.

An exit wave function $\psi(r,R)$ is an exit wave function of radiation as it exits the object 30. This exit wave $\psi(r,R)$ forms a diffraction pattern $\Psi(u)$ at a diffraction plane. Here r is a vector coordinate in real space and u is a vector coordinate in diffraction space.

It will be understood that with both the aperture formed embodiment and the non-aperture embodiment, if the diffraction plane at which scattered radiation is detected is moved nearer to the specimen or object 30 then Fresnel diffraction patterns will be detected rather than Fourier diffraction patterns. In such a case the propagation function from the exit wave $\psi(r,R)$ to the diffraction pattern $\Psi(u)$ will be a Fresnel transform rather than a Fourier transform. It will also be understood that the propagation function from the exit wave $\psi(r,R)$ to the diffraction pattern $\Psi(u)$ may be modelled using other transforms.

In order to select the region of the target object 30 to be illuminated or probed, the lens(es) 20 or aperture may be mounted upon an x/y translation stage which enables movement of the probe function with respect to the object 30. It will also be realised that the object 30 may be moved with respect to the lens(es) or aperture. The probe function 20 may be moved by the translation stage in a grid arrangement of positions. The grid may comprise 20×20 positions, although other numbers of positions may be used and, furthermore, the grid may not comprise equal numbers of positions in both x and y directions. A predetermined offset may be introduced into a location of each grid position. For example, if the grid positions have a pitch of 30 μm, the offset may be ±5 μm. Advantageously, this avoids problems associated with "raster grid pathology".

A detector 40 is a suitable recording device such as a CCD camera or the like which allows the diffraction pattern to be recorded. The detector 40 allows the detection of the diffraction pattern in the diffraction plane. The detector 40 may comprise an array of detector elements, such as in a CCD.

In methods such as those disclosed above, the object and/or radiation source, lens 20 or aperture are moved amongst a plurality of positions. In some embodiments, some of the positions cause the probe function to at least partially overlap that of other probe positions. A diffraction pattern is recorded at each probe position. It has been noted that the accuracy with which the probe position can be determined may limit the accuracy of the image data, which consequently limits a resolution of an image produced using the image data. This problem may be particularly acute with radiation having a relatively short wavelength, such as X-ray and electron radiation, although the present invention is not limited to use with these types of radiation. With such radiation, a target resolution may be <50 nm and accurate determination of the probe position to such accuracy is difficult.

Figure 2:
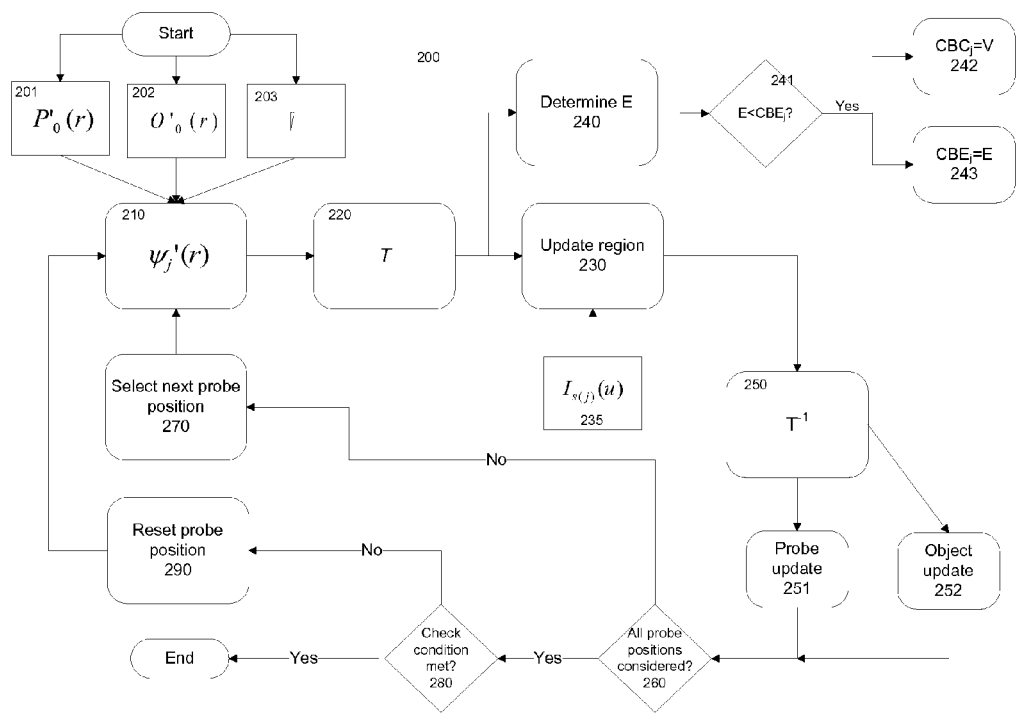
FIG. 2 shows a method according to an embodiment of the invention.

FIG. 2 illustrates a method 200 according to an embodiment of the invention. The method 200 illustrated in FIG. 2 involves simultaneous, step-by-step updating of both probe and object function estimates. However, it will also be realised that embodiments of the invention may be envisaged in which only the object function is updated and a known probe function is used, as in the methods and apparatus disclosed by WO 2005/106531, for example. Furthermore, in other embodiments of the invention, a known object function may be used and the method may determine the probe function. It will also be appreciated that the object function and/or probe function may be updated by other methods.

The method utilises a set s(j) of J diffracted intensities or diffraction patterns, $I_j(u)$, recorded by the detector 40. Each of the J diffraction patterns may be associated with a different probe position. During each iteration of the method, estimates of the probe and object functions are updated for each of the J diffraction patterns measured by the detector 40. An order of considering each of the J measured intensities is chosen. The order may be numerically sequential i.e. j=1, 2, 3 . . . J. In this case, beginning with diffraction pattern s(j) and progressing through to s(J), updated estimates of the probe $P_1'(r) \ldots P_J'(r)$ and object $O_1'(r) \ldots O_J'(r)$ are produced (the dash indicates that these functions are estimates of the true probe and object functions). However, considering the diffraction patterns in a raster fashion (each pattern in a row sequentially and each row sequentially) may cause problems particularly in relation to the estimate of the probe function drifting during the method. Therefore, in some embodiments, the diffraction patterns may be considered in a random or other pseudo-random order. However, for the purposes of explanation, a sequential ordering of the set s(j) will be considered.

For each diffraction pattern, a position of the probe is recorded. In the described embodiments, movement of the probe function is described as being achieved by movement of the object 30. However, it will be realised that the lens 20 or an aperture may alternatively be moved to change the location of the probe with respect to the object 30. The position of the probe for the jth diffraction pattern is denoted as $R_j$, where $R_j=(R_{x,j},R_{y,j})$. $R_{x,j}$ and $R_{y,j}$ are positions of the probe in the x and y axis respectively for the jth diffraction pattern. As noted above, it is likely, and thus assumed, that $R_j$ is inaccurate, at least to some extent. In some embodiments of the invention, it is useful to determine bounds for the inaccuracy of the probe position, although this is not necessary for all embodiments.

In embodiments of the invention, a correction vector is determined for, at least some, or for each probe position. The correction vector for each probe position is determined based upon trial and error application of an offset vector V to the probe function. In some embodiments, a correction vector for each of the J probe positions is determined as a set of J correction vectors (Current Best Correction) $CBC_j$. Each correction vector may be associated with a respective probe position. Each correction vector is determined with respect to an associated error metric. In some embodiments, a set of J error metrics (Current Best Error) $CBE_j$ is determined, as will be explained.

At the start of the method, prior to a first (k=1) iteration, initial probe $P'_0(r)$ 201 and object $O'_0(r)$ 202 functions are determined; the 0 subscripted index indicates that these are initial estimates that will be refined by the method to more closely represent the true functions. The initial probe and object functions 201, 202 may be predetermined initial values, such as initial guesses i.e. pre-calculated approximations, random distributions, or may be based on other initial measurements or prior calculations. The functions 201, 202 are modelled at a number of sample points and are thus represented by matrices. Such matrices can be stored and manipulated by a computer or other such processing unit. Aptly the sample points are equally spaced and form a rectangular array.

An initial offset vector V is determined in step 203. The initial offset vector V may be a predetermined initial value, such as based on an initial guess i.e. a pre-calculated approximation, or may be based on other initial measurements or prior calculations. In some embodiments, the initial offset vector V is determined at least partly in a random or pseudo-random manner. The initial offset vector is, in some embodiments a randomly determined vector V=c(randomx, randomy). It will be understood that the term randomx and randomy determined encompass pseudo-random variants and methods of determining values in a pseudo-random manner. The values randomx and randomy may be selected from a pool of randomly distributed numbers. In some embodiments, to improve the performance of the method, bounds may be placed on the pool of random numbers, or the numbers in the pool may be limited in some other way, such that the method of finding the best $CBC_j$ is improved. The bounds may be a maximum magnitude of the numbers, envisaging that the numbers may be both positive and negative. The value c is a scaling factor value which, in some embodiments, is constant. However, in other embodiments c may be updated, at least periodically, as iterations of the method progress. The value c may be arranged to decrease with increasing numbers of iterations, either linearly or in a step-wise manner. In some embodiments, c may be set to 1 for the k=1 iteration of the method and may be reduced toward zero as k increases. Various schemes for reducing c with increasing numbers of iterations are envisaged. Furthermore, although c may be set to 1 for the k=1 iteration, it may also be set to 1 for the first iteration for which the probe function is offset by the vector V, which may or may not be the k=1 iteration. In some embodiments, offset of the probe function by the offset vector V and determination of the correction vector may only begin after a predetermined number of iterations of the method, for example after k=100 iterations, at which point c may be set to 1. However, for the ease of explanation, embodiments will be described where the offset vector V is used with the probe function in the first k=1 iteration.

In step 210 an estimate of the exit wave $\psi'_j(r)$ that produced the $j^{th}$ diffraction pattern is determined by multiplying the current probe 201 and object 202 estimates. For the first (k=1) iteration of the method, for the first probe position s(1), the initial object estimate $O'_0(r)$ is multiplied by the probe estimate having the initial offset vector V applied $P_0'(r+R_j+V)$ to determine the first exit wave $\psi'_1(r)$. For subsequent iterations of the method, the currently selected estimates of the probe and object functions for the jth probe position i.e. $P'_j(r+R_j+V) \ O_j(r)$ are multiplied to determine the current exit wave $\psi'_j(r)$.

In step 220 the exit wave $\psi_j'(r)$ is propagated to a measurement plane of the detector 40. The propagation produces an estimate $\Psi'_j(u)$ of the wavefront at the plane of the detector 40. The exit wave $\psi_j'(r)$ is propagated to the measurement plane by a suitable transform T, as shown in equation 1. In some embodiments, the transform T may be a Fourier transform, although in other embodiments the transform may be a Fresnel free space propagator. It is also envisaged that other transforms may be used which are suited to the particular application of the method.

$$\Psi'_j(u)=T[\psi'_j(r)] \qquad \text{Equation 1}$$

In step 230 at least a portion of the wavefront $\Psi'_j(u)$ at the plane of the detector 50 is updated based on the measured diffraction pattern $I_{s(j)}(u)$ 235. In some embodiments, the whole i.e. an entire area or extent of the wavefront may be updated, whilst in other embodiments only some of the extent of the wavefront may be updated. As explained in the cited references, since $\Psi'_j(u)$ is a complex-value, it may be written as shown in equation 2:

$$\Psi'_j(u)=A_j(u)\exp(i\phi_j(u)) \qquad \text{Equation 2}$$

In some embodiments, the wavefront $\Psi_j'(u)$ at the plane of the detector 40 may be considered to extend over dM×dN pixels where d is a constant value, for example d may equal 4 and the central M×N pixels correspond to the area of the detector 40. A modulus of this central region of the wavefront may be replaced with Equation 3:

$$\sqrt{I_{s(j)}(u)} \qquad \text{Equation 3}$$

whilst the values of the remaining pixels or matrix positions are left unchanged. In other words, the values of the remaining matrix positions or pixels are allowed to "float". In other embodiments, the modulus of the entire region of the wavefront may be replaced with that from Equation 3.

In step 250 the revised estimate of the wavefront that produced the $j^{th}$ diffraction pattern $\Psi'_j(u)$ is reverse propagated back to a plane of the object 40. The inverse propagation is performed according to the reverse of the transform used in step 220. In some embodiments, the transform used in step 250 is an inverse Fourier transform, although as previously explained other transforms may be used. The inverse transform is performed according to Equation 4:

$$\psi'_{j,new}(r) = T^{-1}[\Psi'_j(u)] \quad \text{Equation 4}$$

In steps 251 and 252 the probe and object functions are updated. The updating provides an improved probe $P'_{j+1}(r)$ and object $O'_{j+1}(r)$ guess. The updating may be performed as described in the incorporated reference WO 201/064051, or by any other method. Similar to WO 201/064051, but also including the offset vector V, the object function may be updated according to Equation 5 and the probe function according to Equation 6:

$$O'_{j+1}(r) = O'j(r) + \alpha \frac{P'^*_j(r+R_j+V)}{|P'_j(r+R_j+V)|^2_{max}}(\psi'_{j,new}(r) - \psi_{j'}(r)) \quad \text{Equation 5}$$

The parameter α governs the rate of change of the object guess. This value may be adjusted between 0 and 2 as higher values may lead to instability in the updated object guess. According to embodiments of the present invention the probe function is reconstructed in much the same manner as the object function. Aptly the probe function guess is carried out concurrently with the update of the object guess. (It will be appreciated that the probe function could optionally be updated more often or less often than the object function).

$$P'_{j+1}(r+R_j+V) = \quad \text{Equation 6}$$
$$P'_j(r+R_j+V) + \beta \frac{O'^*_j(r)}{|O'_j(r)|^2_{max}}(\psi'_{j,new}(r) - \psi_{j'}(r))$$

The result of this update function generates the running estimate for the probe function. The parameter β governs the rate of change of the probe guess. This value may be adjusted between 0 and 2 as higher values may lead to instability in the updated probe guess.

After propagation of the exit wave to the plane of the detector 40 in step 220, an error value E for the $j^{th}$ probe position is determined in step 240. The error value E provides an indication of a difference between the exit wave and the measured diffraction pattern. The error value may be determined according to Equation 7 where $\psi'_j$ is the exit wave which is transformed by the transform T to the measurement plane and $I_j$ is the measured intensity at the measurement plane of the detector 40.

$$E = \frac{\sum_u (|T\psi'_j| - \sqrt{I_j})^2}{\sum_u I_j} \quad \text{Equation 7}$$

It will be realised that other error metric equations may be used which indicate the accuracy of the estimated exit wave $\psi'_j(r)$ with respect to the measured diffraction pattern at the detector 40.

In the first iteration of the method for which the offset vector is applied (k=1 for explanatory purposes), each correction vector (CBC) is set to a predetermined value, such as (0,0). A CBC of (0,0) which does not offset the probe function indicates that a correction vector for the respective probe position has not yet been determined. The corresponding error metric CBE associated with each CBC may also be set to a predetermined initial value. The predetermined value is, in some embodiments, a relatively large value which indicates that the error metric may be improved (reduced) by iterations of the method. In some embodiments, each CBE may initially be set to ∞, although it will be realised that other values may be chosen. Thus, in one embodiment, for the k=1 iteration $CBC_j$=(0,0) and $CBE_j$=∞.

In step 241, the determined error metric E for the current probe position is compared against $CBE_j$ which stores the current best error value for the $j^{th}$ probe position. In the first k=1 iteration, if $CBE_j$=∞ then the determined error metric E will always be less than $CBE_j$, although with other initial values of $CBE_j$ it will be appreciated that this may not always hold true.

Figure 3:
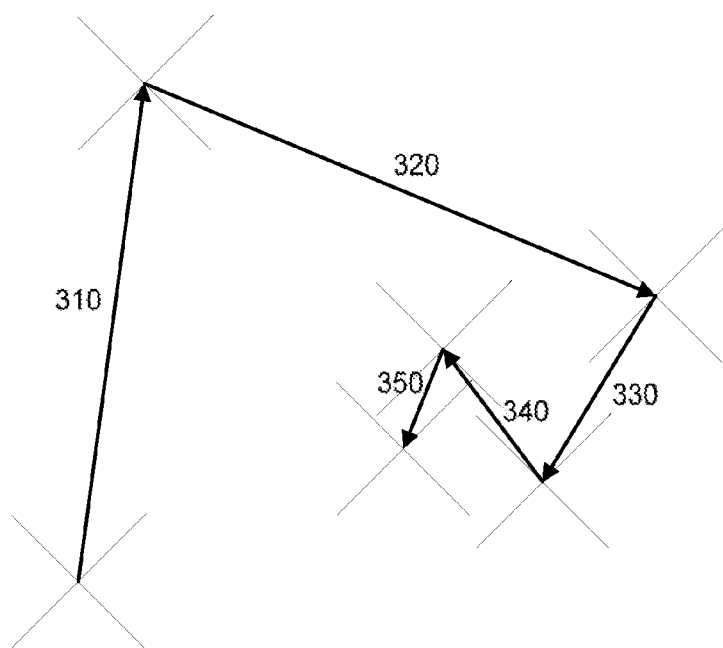
FIG. 3 illustrates a series of correction vectors determined according to an embodiment of the invention.

If E<$CBE_j$ then in step 242 the current best correction vector for the probe position, $CBC_j$, is updated. $CBC_j$ is updated based on the offset vector V applied to the probe position. In step 242, the correction vector $CBC_j$ may set to equal V, since this offset vector has been found to improve the error E. For the first k=1 iteration in an embodiment with an initial value of $CBE_j$=∞, the corresponding vector $CBC_j$ is always set to V, but it will be realised that this depends on the initially chosen value of $CBE_j$. This is illustrated in FIG. 3 as selecting a first correction vector $CBC_j$ 310 for the $j^{th}$ probe position which improves accuracy.

The associated error $CBE_j$ is also updated in step 243 to the determined error value E. Thus, as a result of steps 241-243, if the error E has been improved by use of the vector V, then the current best correction vector and associated error for that probe position are updated. Otherwise, if no improvement has resulted, the vector V is discarded.

It will be realised that the ordering of steps 242 and 243 is not important and that they may be performed in either order or simultaneously.

In step 260 it is determined whether every probe position for the current iteration has been addressed. In other words, it is determined in some embodiments whether j=J. If the current probe position is not the last probe position of the current iteration, then the next probe position is selected. The next probe position may be selected in step 270 by j=j+1. It will also be realised that the next probe position may be randomly selected. However, if the current probe position is the last probe position for the current iteration, then the method moves to step 280.

In step 280 it is determined whether a check condition is met. In some embodiments, the check condition may be determining whether the current iteration number k is a predetermined value, such as k=100 i.e. determining whether a predetermined number of iterations have been performed. Whilst this check is computationally easy, it takes no account of the accuracy of the image data. Therefore, in some embodiments, the check condition compares a current estimate of the diffraction pattern against that recorded by the detector 50. The comparison may be made considering a sum squared error (SSE) as in equation 7:

$$SSE = \sum_j \frac{\sum_u (|T\psi'_j| - \sqrt{I_j})^2}{\sum_u I_j} \quad \text{Equation 7}$$

The method may end when the SSE meets one or more predetermined criteria, such as being below a predetermined value.

If the predetermined criteria is not met, then the method moves to step 290 in preparation for a next iteration (k=k+1) where the probe position is reset i.e. the first probe position is reselected, such as j=1.

In step 275 the offset vector V is updated in preparation for the next probe position to be considered, which may be the first probe position of the next k+1 iteration or the next probe position j+1 of the current iteration. The offset vector is updated based upon the current best correction vector (CBC) for the next probe position to be considered, which has already been selected in step 270 or 290 appropriately. The offset vector V may be updated according to Equation 8.

$$V = CBC_j + c(\text{random}x, \text{random}y) \qquad \text{Equation 8}$$

Where c is a scaling factor and randomx, randomy are random selected values, which may lie within predetermined bounds in the same manner as the initial offset vector was determined in step 203. Thus it will be appreciated that the next offset vector V to be considered is at least partly based on the current best correction vector CBC found for the respective probe position. Based on the updated offset vector V it is then considered whether the additional randomly determined element of the offset vector improves the error metric E. In this way, the current best correction vector gradually tracks toward a vector which improves the accuracy of exit wave determination, leading to improved object and/or probe function guesses.

Referring again to FIG. 3, it is illustrated how, in subsequent iterations of the method, the current best correction vector (CBC) for a particular probe position $CBC_j$ gradually seeks an optimum correction vector. The correction vector may be updated in the first k=1 iteration, as described, with a first correction vector 310. Following the update in the first iteration, the correction vector may not be updated in each iteration of the method. If application of the vector V does not improve the error $CBE_j$ associated with at probe position, then the correction vector $CBC_j$ is not updated in that iteration. FIG. 3 shows a series of correction vectors 310, 320, 330, 340, 350 which are each successively, but not necessarily in consecutive iterations of the method, improve the accuracy of probe position determination. It can be seen how the correction vector is updated to gradually home-in on an improved correction vector, particularly if the scaling value c is gradually reduced since the magnitude of the randomly determined element of the offset vector V is gradually decreased.

Figure 4:
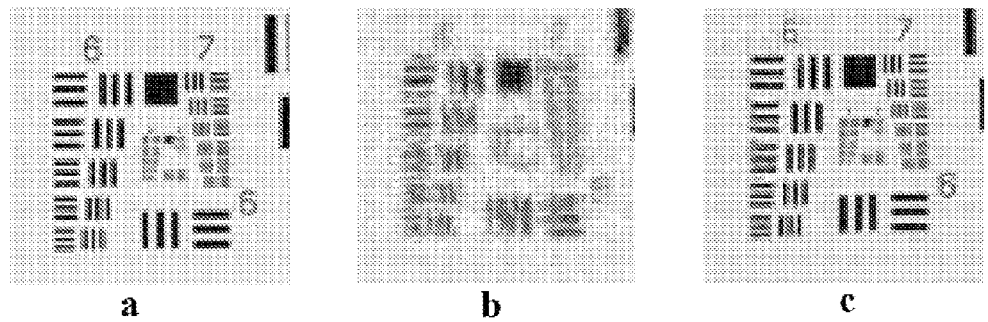
FIG. 4 shows images of a resolution test pattern generated from image data produced by embodiments of the invention.

FIG. 4 illustrates an improvement in resolution of image data produced by embodiments of the present invention. FIG. 4(a) is an image of a resolution test pattern, where the positions of the specimen are well characterised i.e. at a known position subject to low position error. FIG. 4(b) is an image reconstructed from the same data, where random errors have been introduced into the measured specimen positions representing poor positioning accuracy. As can be observed, the resulting image is of lower quality than FIG. 4(a). FIG. 4(c) is an image after correcting for these position errors present in FIG. 4(b) using an embodiment of the present invention. It will be noted that the resolution of the image in FIG. 4(c), which is indicated by the smallest visible line features, matches that of the optimal result shown in FIG. 4(a), although some additional noise may however remain present in the image shown in FIG. 4(c).

Figure 5:
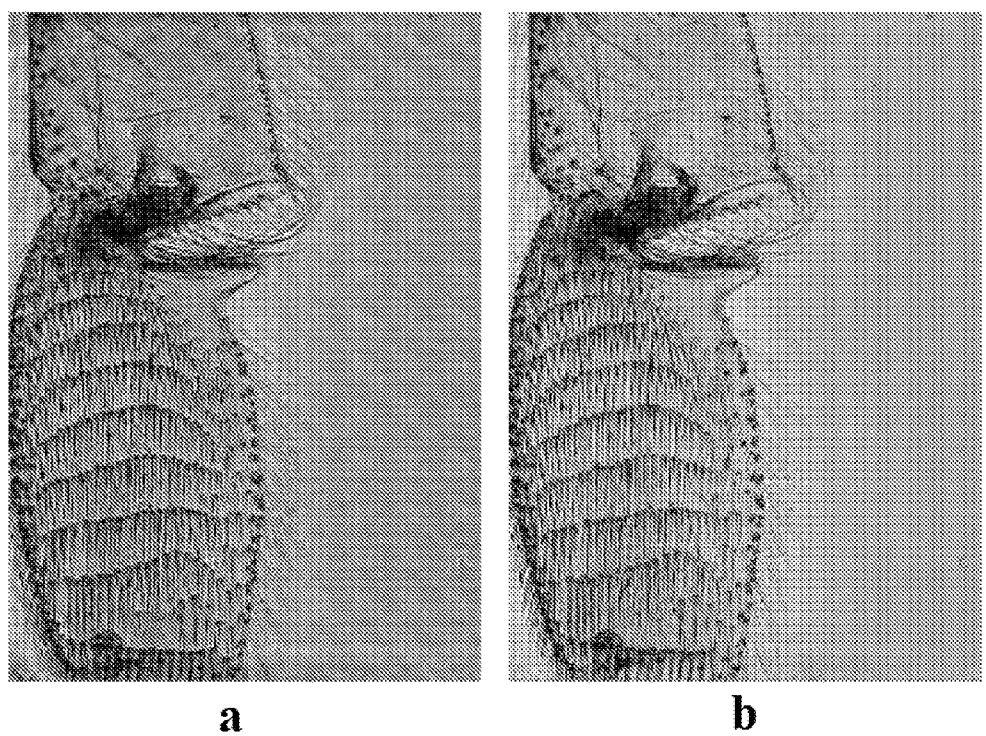
FIG. 5 shows images of a bee's hind leg showing an effect of embodiments of the present invention.

FIG. 5(a) shows an image of a bee's hind leg obtained by a ptychographic experimental method. A translation stage of poor accuracy was used to carry out the experiment from which this image resulted, leading to the mottled noise pattern seen in the clear area to the right of the bee's leg, and poorly defined features, such as hairs, within the leg itself. FIG. 5(b) is an image reconstructed from the same data using an embodiment of the invention. It can be observed that both the clear area and the structure of the bee's leg have been significantly improved in FIG. 5(b).

Figure 6:
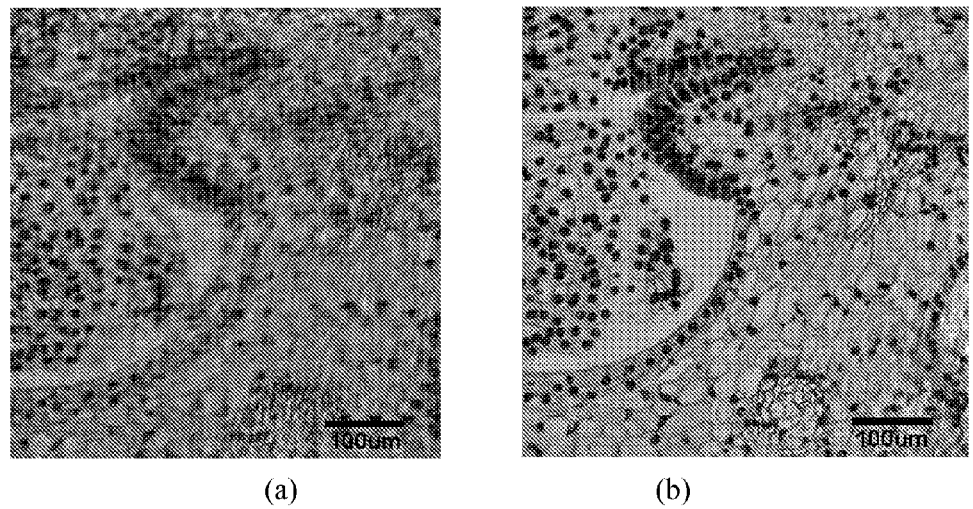
FIG. 6 shows further images showing the effect of embodiments of the present invention.

FIG. 6(a) illustrates an image produced using image data obtained with a subject (lily pollen) supported on an optical bench which suffers from backlash. The optical alignment for this experiment was imperfect. FIG. 6(b) shows an image produced of the same subject after position correction according to an embodiment of the invention where it can be seen that the quality of the image has improved.

Figure 7:
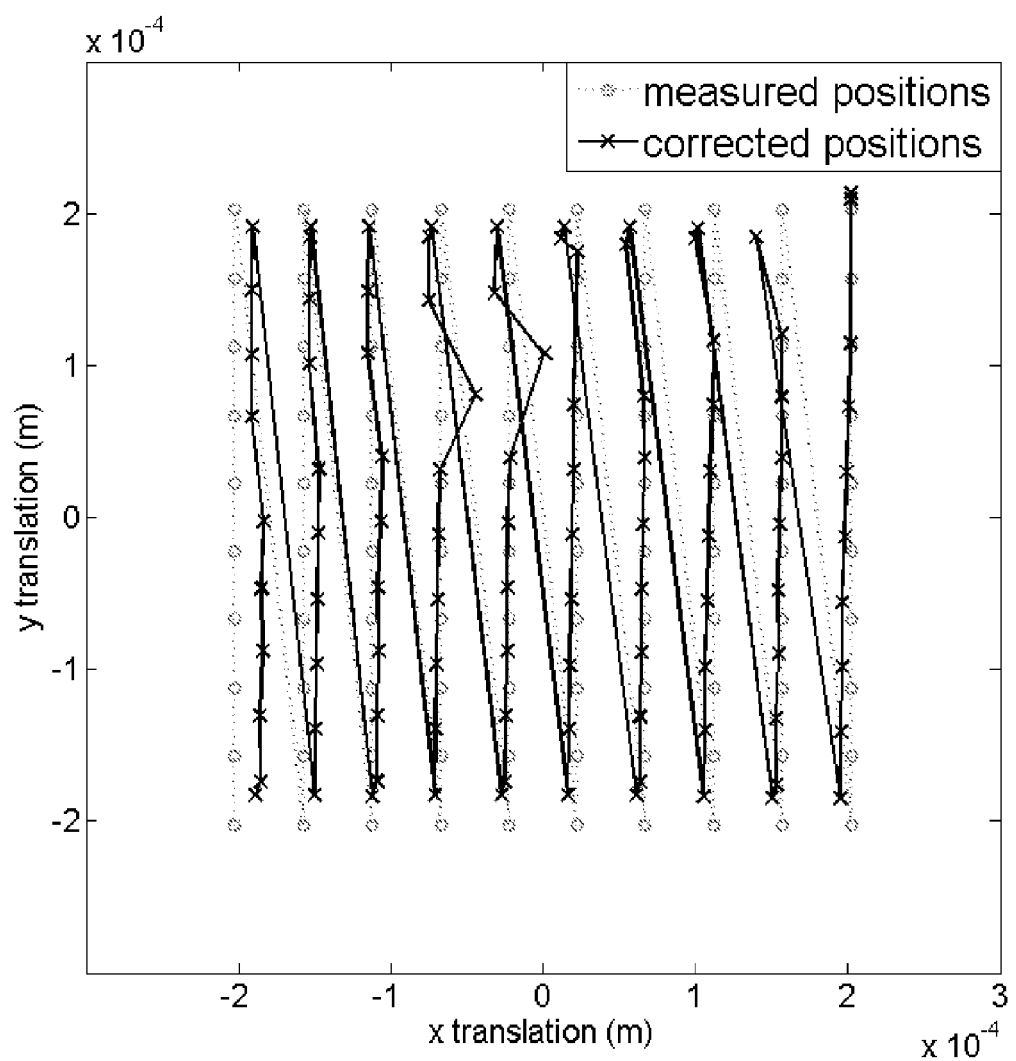
FIG. 7 is a plot of position data showing the effect of embodiments of the present invention.

Referring to FIG. 7, an experiment was carried out on an optical bench using a poorly aligned system and a motorised translation stage with a pronounced backlash. The stage was programmed to translate over a raster grid of 10×10 positions; this raster grid was used to form the 'measured positions' (dashed) plot in the figure. The poor alignment of the optical components and the backlash of the translation stage lead to inaccuracies in these positions such that the ePIE produced a heavily distorted reconstruction, the modulus of which is shown in FIG. 6(a) (the phase part of the reconstruction was similarly distorted). Feeding the same data into an embodiment of the invention produced corrected translation positions as shown in the 'corrected positions' (solid) plot in the figure. An analysis of these positions shows that they are rotated and scaled relative to the measured positions, therefore correcting errors expected from the poor alignment of the optical components, and that they also exhibit a skew, correcting for the stage backlash. The significantly improved reconstruction that these corrected positions produce is shown in FIG. 6(b) (the modulus is shown—the phase image is similarly improved)

In the previously described embodiments, an offset vector V is determined and the effect of the application of the offset vector to the wavefront based thereon is compared against the current best correction vector for that probe position ($CBC_j$). However, in some embodiments of the invention for each probe position and iteration of the method more than one offset vector is determined and a respective number of wavefronts are calculated based on each of the offset vectors. Advantageously, by considering, during each iteration, more than one offset vector for each probe position the method may determine an accurate current best correction vector more quickly.

In these embodiments, in step 203 a set comprising a plurality of initial offset vectors are determined. The set may comprise m=1 . . . M initial offset vectors $V_m$. Each of the set of vectors may be determined as previously explained with reference to FIG. 2.

In step 210 a plurality of estimates of exit waves are determined. An estimated exit wave is determined for each of the set of offset vectors. Thus M exit waves are determined for each probe position as:

$$\psi'_{j,m}(r) = P'_{j,m}(r + R_j + V_m) O_j(r)$$

In step 220 each of the plurality of exit waves is forward-propagated to the measurement plane of the detector 40 to provide M estimates of the wavefront incident upon the detector 40 $\Psi_{j,m}'(u) = T[\psi'_{j,m}(r)]$ as previously described.

In step 240 the modulus of each $\Psi_{j,m}'(u)$ is compared against $\sqrt{I_j}$, as in equation 7 previously described, to provide a set of errors $E_m$ each indicating a difference between the wavefront with the respective vector applied and the measured intensity at the measurement plane. Once the set of errors has been determined a lowest error in the set is determined. An index of the minimum value of $E_m$ is n such that:

$$n = \underset{m}{\mathrm{argmin}} E_m$$

The lowest error $E_m$ may then be compared against the current best error for that probe position $CBE_j$ as in step 241 to determine whether the current best correction vector $CBC_j$ and current best error $CBE_j$ should be updated as in steps 242, 243.

Once the wavefront having the lowest associated error metric has been determined, at least a portion of the estimated wavefront at the plane of the detector having the lowest error is updated based on the measured diffraction pattern as in step 230 described above.

In this way, multiple (M) potential correction vectors are considered for each probe position during each iteration and a result of the best of the M correction vectors is compared against the current best correction vector CBC for that probe position. This results in a faster determination of a given level of accuracy of current best correction vector.

Embodiments of the invention may also correct for global positioning errors. Global positioning errors may be caused, for example, by a relative rotation of the positioning stage and the detector, inaccurate measurement of the specimen-detector distance which causes a scaling error, or a linear drift during data acquisition. In this sense, the term "global" is understood to be an error which is applied to all probe positions, although each probe position may also be subject to a "local" error specific to that probe position, as previously described In such embodiments of the invention the previously described offset vector V is referred to as $V_{l,j}$ wherein the subscript l indicates that the vector is for correction of a local error associated with the probe position j. Additionally one or both of correction scalars $C_r$ and $C_s$ are introduced, wherein $C_r$ is a rotation correction factor and $C_s$ is a scaling correction factor. As in previously described embodiments, for a first iteration for which the offset vector and correction factors are introduced, such as the k=1 iteration, they are initially set to a predetermined value, which may be zero. In an embodiment including correction for both global rotation and scaling as a result of the method $C_r$ represents an angle to correct for a global rotation, which may be stored in radians, $C_s$ represents a scaling factor and $V_{l,j}$ a correction vector for each probe position.

Embodiments of the invention may be envisaged where only a single group of correction vector $V_{l,j}$ and correction factors $C_r$ and $C_s$ are considered for each probe position during each iteration. However, for the purposes of explanation, an embodiment will be explained where a set of M groups of vectors $V_{l,j}$ and correction factors $C_r$ and $C_s$ are considered. A combined offset $C_{j,m}^{tot}$ is determined by trial and error according to:

$$C_{j,m}^{tot} = CBC_{l,j} + c_l \Delta_{l,m} + R_j \begin{bmatrix} \cos(C_r + c_r \delta_{r,m}) - 1 \\ \sin(C_r + c_r \delta_{r,m}) - 1 \end{bmatrix} + R_j(C_s + c_s \delta_{s,m})$$

For comparison with earlier embodiments, it will be recalled that the offset vector V=c(randomx, randomy). In the above equation $c_l$ is the previously described offset value c and $\Delta_{l,m}$ is a vector of two random numbers (randomx, randomy). $c_l \Delta_{l,m}$ may have a value in a predetermined range, such as the range ±1. The variables $c_l$, $c_r$ and $c_s$ are scaling values which may be reduced as iterations of the method progress, either linearly or step-wise, as previously explained. The scaling values may decrease independently i.e. according to a different number of iterations and/or rate to a small or zero value. In some embodiments, the vectors $R_j$ have mean x and y values equal to 0. If the position grid is centred around another value then the rotation and scaling may result in a large global translation which increases the size of the matrices representing the object and probe functions unnecessarily. Thus the combined offset $C_{j,m}^{tot}$ includes correction for local probe position error, global rotation and global scaling.

Thus M wavefronts are calculated according to:

$$\psi'_{j,m}(r) = P'_j(r + R_j + C_{j,m}^{tot}) O'_j(r)$$

The method proceeds as previously described to find a combined offset $C_{j,m}^{tot}$ of the set of M offsets having a lowest error. If the error is lower than the current best correction vector $CBC_j$ for that probe position then $CBC_j$ and the global scalars $C_r$ and $C_s$ are updated in step 242 as:

$$CBC_{l,j} \leftarrow CBC_{l,j} + c_l \Delta_{l,m}$$

$$C_r \leftarrow C_r + c_r \delta_{r,m}$$

$$C_s \leftarrow C_s + c_s \delta_{s,m}$$

Embodiments of the invention may be envisaged which determine correction factors for other global errors, such as global drift. In these embodiments, further scalars such as $C_d$ are included in the calculation of the combined offset $C_{j,m}^{tot}$ as, for example:

$$\left(j - \frac{J}{2}\right) C_d + c_d \delta_{d,m}$$

The factor J/2 in the above equation ensures that drift does not introduce a large global translation which increase the size of the matrices representing the object and probe functions unnecessarily. In some embodiments the J/2 term may be omitted or may be a different value.

Figure 8:
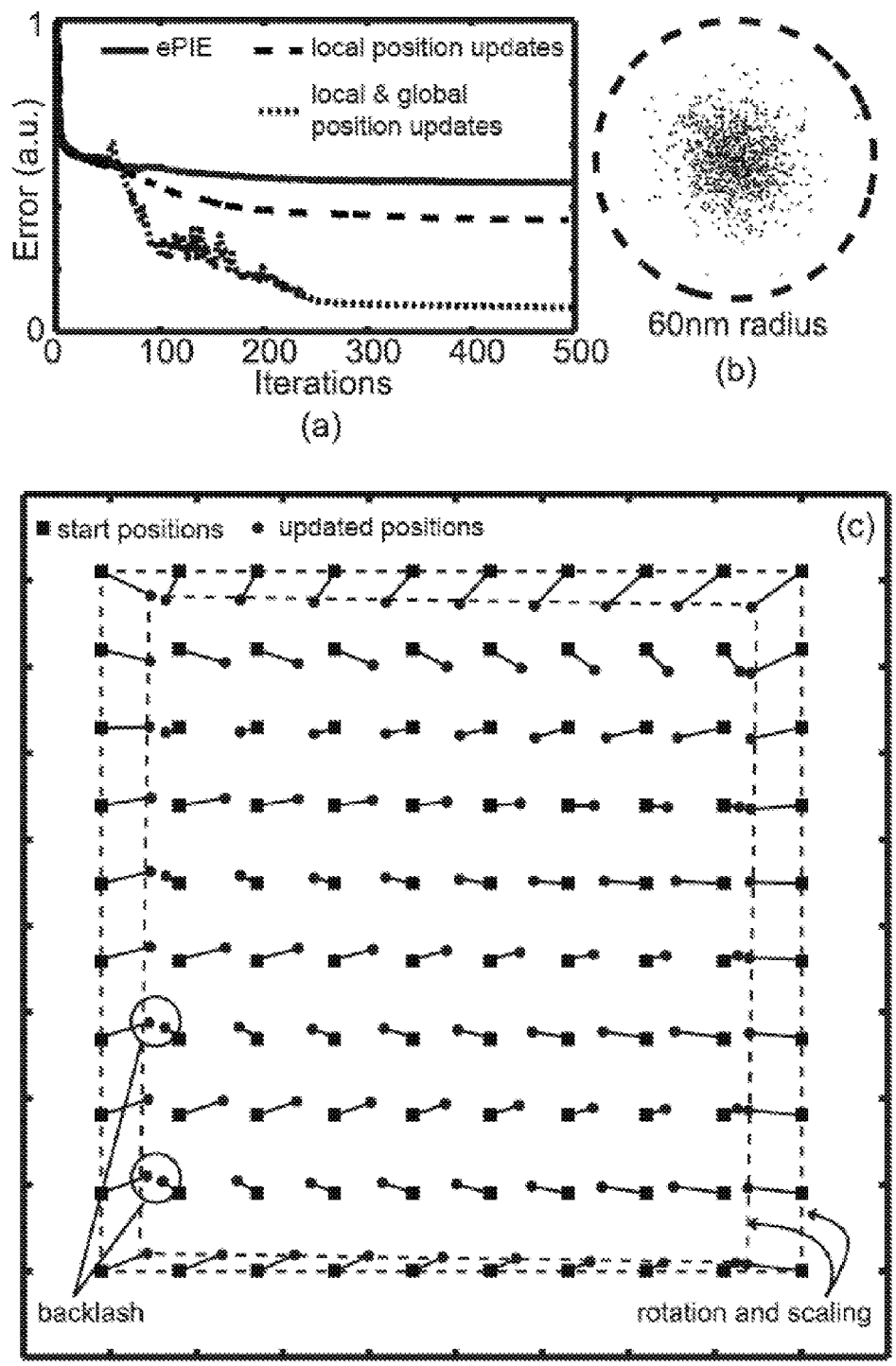
FIG. 8 illustrates the performance of embodiments of the invention.

FIG. 8 illustrates the correction of position errors by embodiments of the present invention.

FIG. 8(a) illustrates the performance of a prior art ePIE embodiment, shown in FIG. 8(a) as diffraction pattern error, against an embodiment in which only a local position error is corrected, and an embodiment in which global rotation and scaling are also corrected. As can be appreciated, correction of only local position error improves upon the prior art ePIE method, whilst additional correction for rotation and scaling improves still further.

The performance is plotted over 500 iterations of the methods. Correction of only local error reduces the error level by around 20-25% against the prior art ePIE method. It can be observed that the error associated with correction of both local and global errors initially increases, denoted by the spike once error correction is introduced after 50 iterations, followed by large fluctuations in the error level until the values of $c_r$ and $c_s$ are reduced to 0 after 250 iterations. The fluctuation in the error level benefits embodiments of the invention because convergence of the algorithm is able to escape local minima and to correct for global errors.

FIG. 8(b) illustrates a performance of a plurality of runs (operations) of an embodiment of the invention including both local and global position correction. For 10 runs each calculating 10 correction vectors for each of 100 positions, the plot compares these sets of 10 corrections to their means and shows that the same position is determined to within 60 nm (0.04 pixels) for each of the 10 runs.

FIG. 8(c) shows a graph of the corrections made to probe positions showing how rotation, scaling and backlash errors are corrected. Backlash is a positioning error resulting from a change in direction of a translation stage, e.g. from left to right or from up to down.

Figure 9:
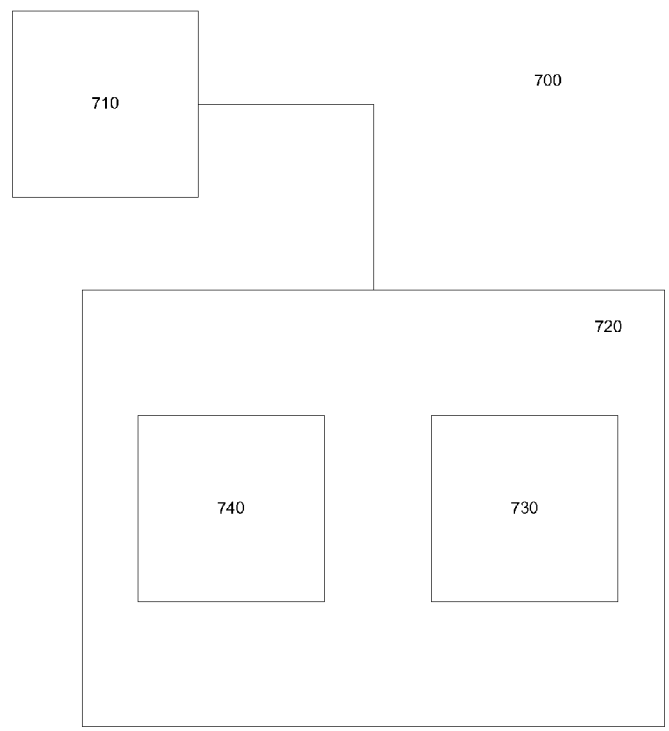
FIG. 9 illustrates an apparatus according to an embodiment of the invention.

FIG. 9 illustrates an apparatus 700 according to an embodiment of the invention. The apparatus 700 is arranged to determine image data for an object. The image data may, in some embodiments, be used to generate a visible image of the object. The visible image may, for example, be output to a display device.

The apparatus 700 comprises a detector 710 for detecting an intensity of radiation falling thereon. The detector 710 corresponds to the detector 50 shown in FIG. 1 arranged to record a diffraction pattern formed by radiation scattered by the target object. The detector may comprise a plurality of detecting elements each capable of outputting a signal indicative of the intensity of radiation falling thereon. The detector may be a CCD device, or similar. The detector 710 is communicably coupled to a processing unit 720 which is arranged to determine the image data based on the radiation intensity detected by the detector 710. The processing unit 720 comprises a memory 730 and a data processor 740, such as a CPU. Although FIG. 7 shows the processing unit 720 comprising one memory, the processing unit 720 may comprise two or more memories. Furthermore, although shown as comprising one data processor, the processing unit 720 may comprise more than one data processor 740, and each data processor may comprise one or more processing cores. The memory 730 may be arranged to store measured radiation intensity data $I_{s(j)}(u)$ corresponding to a plurality of probe positions. The data processor 740 may implement a method according to an embodiment of the invention, such as that shown in FIG. 2 and previously described. The data processor may store determined image data in the memory 730.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine readable storage storing such a program. Still further, embodiments of the present invention may be conveyed electronically via any medium such as a communication signal carried over a wired or wireless connection and embodiments suitably encompass the same.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. A method of providing image data for constructing an image of a region of a target object, comprising:
    detecting, by at least one detector of a diffractive imaging device, at least a portion of radiation scattered by the target object with the incident radiation or an aperture at a predetermined probe position;
    determining, by a processing unit, an offset vector for reducing an error associated with the probe position;
    estimating, by the processing unit, a wavefront based on a probe function having the offset vector applied to the probe position; and
    providing via an iterative process image data responsive to the detected radiation.

2. The method of claim 1, comprising:
    updating a current best offset vector associated with the probe position when a current best error metric associated with the probe position is improved.

3. The method of claim 2, wherein the updating of the current best offset vector comprises:
    determining an error metric for the offset vector based on a difference between the estimated wavefront and a wavefront corresponding to the radiation detected by the at least one detector; and
    comparing the error metric for the offset vector with a current best error metric associated with the current best offset vector for the probe position.

4. The method of claim 1, comprising:
    determining an offset vector for each of a plurality of probe positions.

5. The method of claim 1, wherein the offset vector is determined in an at least partly random manner.

6. The method of claim 1, comprising:
    determining a plurality of offset vectors;
    estimating a plurality of wavefronts based on a probe function each having a respective one of the offset vectors applied to the probe position; and
    selecting one of the plurality of offset vectors having a lowest associated error.

7. The method of claim 6, wherein the plurality of offset vectors are determined during each iteration of the method.

8. The method of claim 1, comprising:
    determining one or more global correction factors for correcting one or more errors associated with a plurality of probe positions.

9. The method of claim 8, wherein the global correction factors correct for one or more of scaling, drift and rotation.

10. The method of claim 1, wherein the, or each, offset vector is determined in a trial-and-error manner.

11. The method of claim 1, wherein the method is performed iteratively and the offset vector is determined during a plurality of iterations of the method.

12. The method of claim 11, wherein the offset vector is first applied to the probe function during a second or greater iteration of the method.

13. The method of claim 2, wherein the current best offset vector is an offset vector having an associated current best error metric according to one or more predetermined criteria.

14. The method of claim 13, wherein the one or more predetermined criteria includes a lowest current best error metric.

15. The method of claim 11, wherein the offset vector is determined at least in part according to a scaling factor such that a magnitude of the offset vector is reduced with increasing iterations of the method.

16. The method of claim 2, wherein the offset vector is determined based on the current best offset vector.

17. The method of claim 2, wherein the offset vector V is determined according to:

$$V = CBC + (\text{randomx}, \text{randomy})$$

wherein CBC is the current best offset vector for the probe position and randomx and randomy are randomly determined coordinates.

18. The method of claim 3, wherein the error metric E is determined according to the equation:

$$E = \frac{\sum_u (|T\psi'_j| - \sqrt{I_j})^2}{\sum_u I_j}$$

wherein $\psi'_j$ is an exit wave determined for a jth probe position, T is a transform for transforming the exit wave to a plane of the at least one detector and $I_j$ is a measured intensity at the measurement plane of the at least one detector.

19. An apparatus for providing image data for constructing an image of a region of a target object, comprising:
a data store storing data indicating an intensity of detected radiation scattered by the target object and detected by a detector of a diffractive imaging device with the incident radiation or an aperture at a predetermined probe position;
a processing means arranged to determine an offset vector for reducing an error associated with the probe position, to estimate a wavefront based on a probe function having the offset vector applied to the probe position, and to provide via an iterative process image data responsive to the detected radiation.

20. The apparatus of claim 19, wherein the processing means is arranged to update a current best offset vector associated with the probe position when a current best error metric associated with the probe position is improved.

21. The apparatus of claim 20, wherein the processing means is arranged to:
determine an error metric for the offset vector based on a difference between the estimated wavefront and a wavefront corresponding to the data indicating an intensity of radiation held in the data store, and
to compare the error metric for the offset vector with a current best error metric associated with the current best offset vector for the probe position.

22. The apparatus of claim 19, wherein the processing means is arranged to determine an offset vector for each of a plurality of probe positions.

23. The apparatus of claim 19, wherein the processing means is arranged to perform operations comprising:
determining a plurality of offset vectors;
estimating a plurality of wavefronts based on a probe function each having a respective one of the offset vectors applied to the probe position; and
selecting one of the plurality of offset vectors having a lowest associated error.

24. The apparatus of claim 19, wherein the processing means is arranged to perform operations comprising:
determining one or more global correction factors for correcting one or more errors associated with a plurality of probe positions.

25. The apparatus of claim 24, wherein the global correction factors correct for one or more of scaling, drift and rotation.

26. The apparatus of claim 19, wherein the offset vector is determined in an at least partly random manner.

27. The apparatus of claim 19, wherein the processing means is arranged to determine, estimate, and provide iteratively and the offset vector is determined during each of a plurality of iterations.

28. The apparatus of claim 27, wherein the offset vector is first applied to the probe function during a second or greater iteration.

29. The apparatus of claim 20, wherein the current best offset vector is an offset vector having an associated current best error metric according to one or more predetermined criteria.

30. The apparatus of claim 29, wherein the one or more predetermined criteria includes a lowest current best error metric.

31. The apparatus of claim 27, wherein the offset vector is determined at least in part according to a scaling factor, such that a magnitude of the offset vector is reduced with increasing iterations.

32. A computer program tangibly stored on a non-transitory recording medium, which, when executed by a computer, is arranged to perform the method of claim 1.

* * * * *